US008891243B2

(12) United States Patent
Tanaka et al.

(10) Patent No.: US 8,891,243 B2
(45) Date of Patent: Nov. 18, 2014

(54) WALL MOUNTED DIAGNOSTIC CABINET ASSEMBLY

(75) Inventors: Kazuna Tanaka, Cos Cob, CT (US);
Jeffrey Kapec, Westport, CT (US);
Yukiko Naoi, New York, NY (US)

(73) Assignee: Tanaka Kapec Design Group, Inc., Norwalk, CT (US)

( * ) Notice: Subject to any disclaimer, the term of this patent is extended or adjusted under 35 U.S.C. 154(b) by 316 days.

(21) Appl. No.: 13/385,995

(22) Filed: Mar. 20, 2012

(65) Prior Publication Data

US 2012/0243183 A1    Sep. 27, 2012

Related U.S. Application Data

(60) Provisional application No. 61/457,422, filed on Mar. 23, 2011.

(51) Int. Cl.
*G06F 1/16* (2006.01)
*A61B 19/02* (2006.01)

(52) U.S. Cl.
CPC ..... *A61B 19/0248* (2013.01); *A47B 2200/0066* (2013.01); *A61B 2019/0249* (2013.01)
USPC ........................................ 361/724; 312/293.3

(58) Field of Classification Search
USPC .................. 361/724; 312/293.3; 439/719
See application file for complete search history.

(56) References Cited

U.S. PATENT DOCUMENTS

| 3,702,456 | A  | * | 11/1972 | Patton ........................ 439/404 |
| 7,037,143 | B2 | * | 5/2006  | Aziz et al. .................... 439/719 |
| 7,734,372 | B2 | * | 6/2010  | Shoenfeld .................... 700/237 |
| 7,915,542 | B2 | * | 3/2011  | Forbis ......................... 174/480 |
| 8,446,723 | B2 | * | 5/2013  | Goza ........................... 361/692 |
| 2003/0008568 | A1 | * | 1/2003 | Follingstad et al. ......... 439/719 |
| 2003/0076015 | A1 | * | 4/2003 | Ehrenreich et al. ......... 312/209 |
| 2003/0119385 | A1 | * | 6/2003 | Elliot et al. .................. 439/894 |
| 2007/0069614 | A1 | * | 3/2007 | Waugh et al. ................ 312/245 |
| 2007/0126318 | A1 | * | 6/2007 | Hamberg et al. ............ 312/209 |
| 2007/0159035 | A1 | * | 7/2007 | Mullen ......................... 312/245 |
| 2007/0244598 | A1 | * | 10/2007 | Shoenfeld .................... 700/236 |
| 2007/0252919 | A1 | * | 11/2007 | McGreevy .................... 348/825 |
| 2009/0066204 | A1 | * | 3/2009 | Reina et al. ................. 312/223.1 |
| 2009/0212671 | A1 | * | 8/2009 | Clark et al. ................... 312/209 |
| 2010/0148647 | A1 | * | 6/2010 | Burgess et al. .............. 312/327 |
| 2010/0289392 | A1 | * | 11/2010 | DeWeerd ..................... 312/245 |
| 2012/0212112 | A1 | * | 8/2012 | Reina et al. ................... 312/209 |
| 2012/0218701 | A1 | * | 8/2012 | Thomas .................... 361/679.22 |

* cited by examiner

*Primary Examiner* — Lisa Lea Edmonds
(74) *Attorney, Agent, or Firm* — John S. Hale; Gipple & Hale

(57) ABSTRACT

A cabinet assembly for holding electronic instruments comprising a mounting rail defining a channel therein, the mounting rail defining a plurality of spaced apertures and center cutouts and a chassis coupler mounted to mounting rail. A housing is mounted to the chassis coupler and an exterior housing cover is mounted to the housing. The mounting rail is covered by a rail cover panel having wiring raceways and an access cover panel is mounted at the base of the rail cover panel.

19 Claims, 6 Drawing Sheets

Fig. 2
Fig. 3
Fig. 4
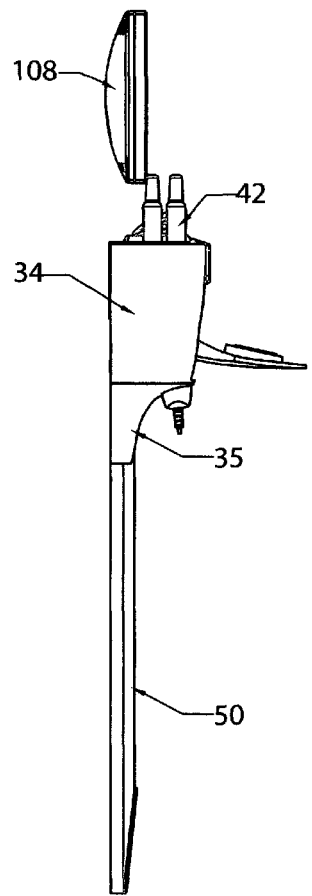
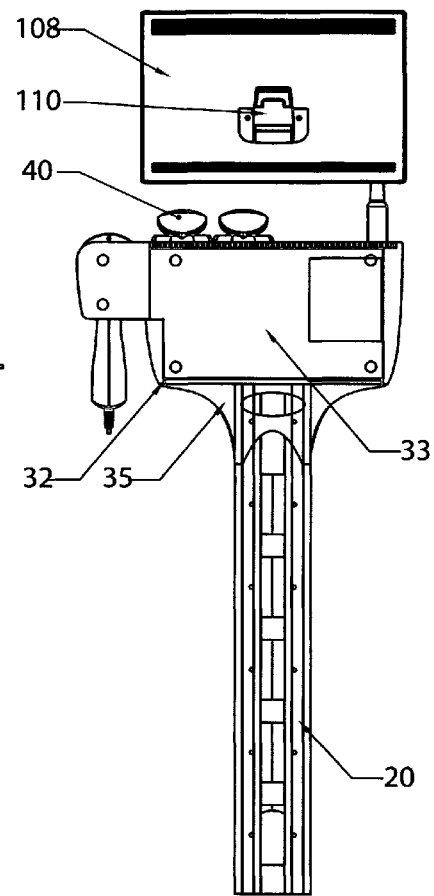
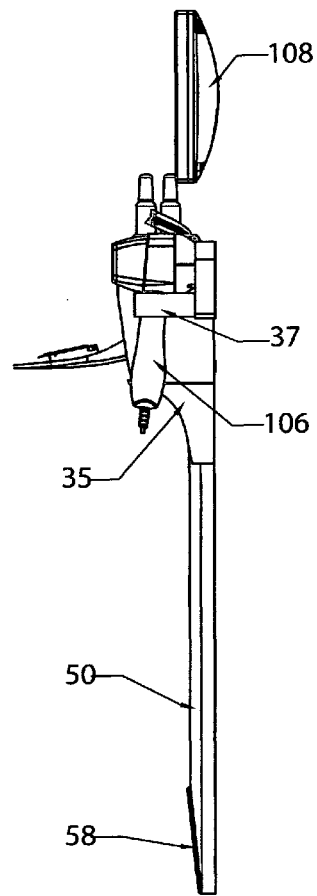

Fig. 6
Fig. 7
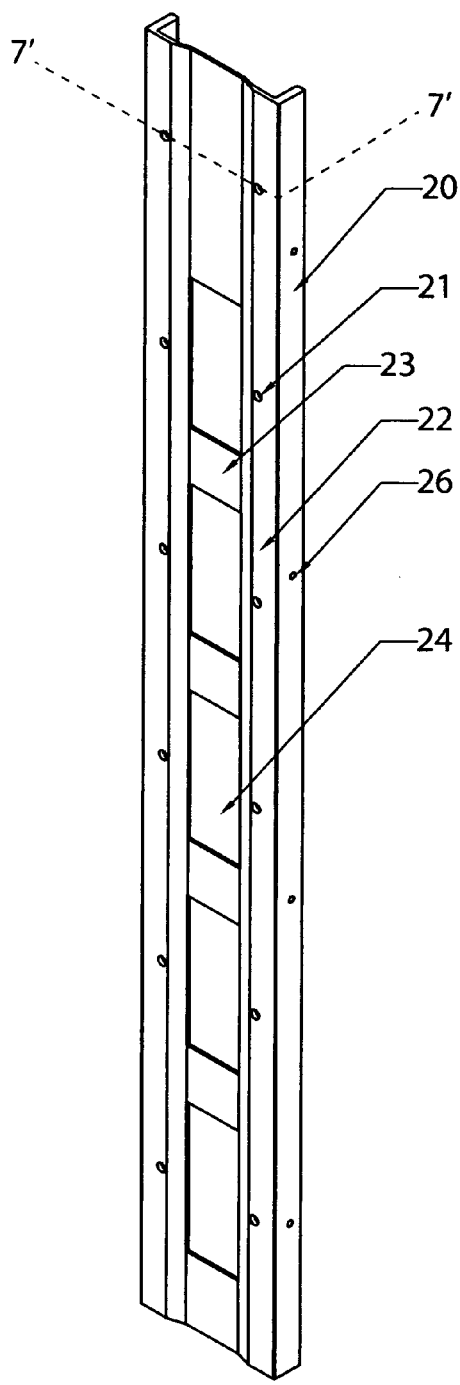
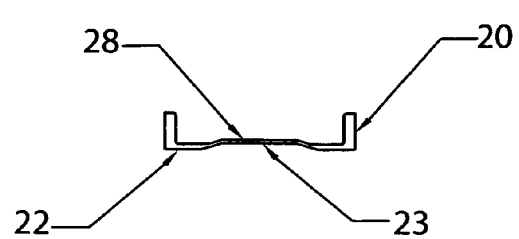

WALL MOUNTED DIAGNOSTIC CABINET ASSEMBLY

RELATED APPLICATIONS

This application claims priority and benefit from U.S. Provisional Patent Application No. 61/457,422, filed Mar. 23, 2011.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention relates to a cabinet assembly for holding and displaying electronic medical equipment 2. Description of the Prior Art In the present medical office and hospital environment the use of computer driven diagnostics is acquiring an ever expanding role. Such computer and related monitoring equipment is commonly mounted to the wall of the treatment room.

Medical monitoring systems typically include multiple electronic components such as computers, keyboards, display screens, power supplies, probes, security verifiers and other items. The physical presence of these components may obstruct access to people or things. In addition, the monitoring system components with their accompanying cabling may impede access to a patient or block traffic flow through a confined area or simply present safety hazards. Shelving which is commonly used for holding such components has significant drawbacks as to appearance and usage.

One of the problems with wall mount devices is that wall mount requirements vary from device to device. The primary requirement is the need to secure the unit to the wall surface. Problems arise as the wall surface can be irregular, rough or smooth and may be constructed with differing materials such as cement block, wood paneling, sheet rock, sheet metal, ceramic or a multitude of other materials. With each of these variables, a contractor must evaluate the wall composition and determine the best method for mounting the device to the specific wall construction and how the same can then be connected to a power connection. Currently a power line is run from an outlet along the baseboard and then up the wall in an exposed condition to the unit. However, a growing number of building codes may not permit a device to be wired in this manner. An alternative approach is to require an electrician to hard wire the device. This process is involved and expensive in terms of running an electric line through the wall and installing an outlet box in the exact place where the unit will be mounted. Once this mounting is done the placement is fixed. While this may be acceptable in a hospital setting, a private practitioner may want more flexibility in placement of the device.

In the present invention the apparatus is installed midway on the wall in a hallway of the hospital outside a patient room or in each patient room or in a physician's office. The apparatus may additionally be installed in selected examination rooms.

Thus, there are a number of practical difficulties which are resolved by the present invention.

SUMMARY OF THE INVENTION

The present invention provides for a wall mounted instrument cabinet assembly which is mounted to a wall through the use of a vertically oriented support rail defining a channel therein, the support rail defining a plurality of spaced cutouts which fit over power outlets with the channel formed by the support rail providing storage for power cabling and the like. A housing coupler mechanism is mounted on the top of the support rail and an instrument support housing is mounted to said housing coupler mechanism. The support housing can be provided with a drop down panel pivotally mounted to the housing allowing the panel to drop down to a position substantially horizontal to a floor allowing a keyboard to a computer to be accessed and used or it may be used as a work surface or writing surface. The support housing is covered by an exterior cover removably mounted to the support housing and a cover plate is mounted over the support rail to cover said support rail and power lines and digital or optical communication lines contained therein.

It is an object of the invention to provide a self contained unit which includes an assembly of the necessary diagnostic instruments allowing easy access and use by nurses, technicians and physicians.

Another object of the present invention provides an instrument cabinet which can be easily installed on any wall surface at any desired height.

It is still another object of the invention to provide an instrument cabinet which covers all power cables and communication lines for the instruments stored therein.

It is yet another object of the invention to provide an instrument cabinet which allows easy access to power cables, and the instruments contained therein.

These and other objects, advantages, and novel features of the present invention will become apparent when considered with the teachings contained in the detailed disclosure along with the accompanying drawings.

BRIEF DESCRIPTION OF THE DRAWINGS

The present invention will be described with reference to the appended Figures, in which:

FIG. 2 is a side elevation view of the wall mount cabinet of FIG. 1;

FIG. 3 is a front elevation view of the wall mount cabinet assembly of FIG. 1 with the support rail cover removed;

FIG. 4 is an opposite side elevation view of the wall mount cabinet assembly of FIG. 2;

FIG. 6 is an enlarged perspective view of the support rail shown in FIG. 5;

FIG. 7 is a cross section of the support rail taken across FIG. 6 at line 7'-7';

DESCRIPTION OF THE INVENTION

Figure 1:
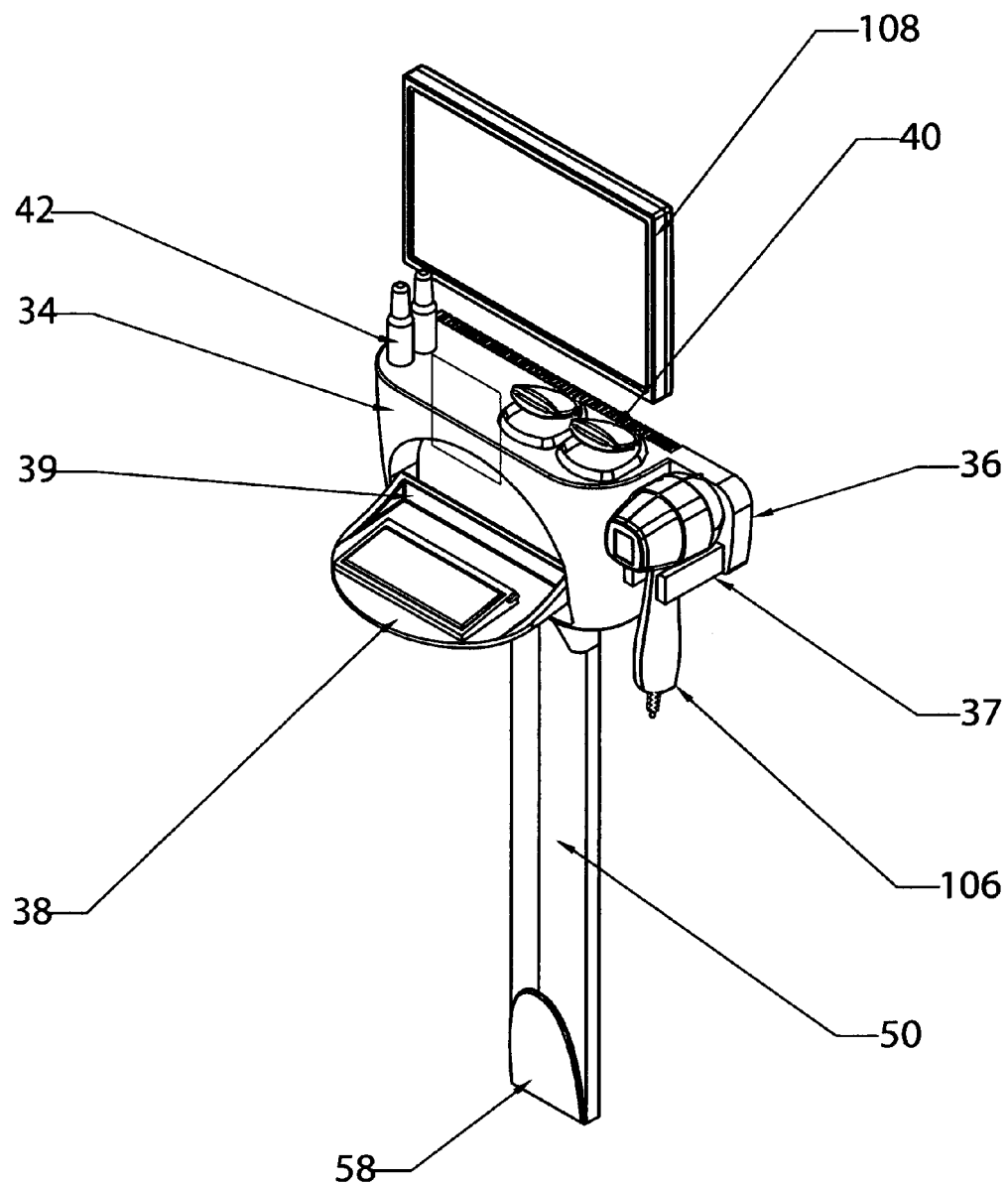
FIG. 1 illustrates a perspective view of the inventive wall mount cabinet assembly.

The present invention is directed towards a wall mounted diagnostic cabinet assembly 10 for use in medical office and hospital environments.

The preferred embodiment and best mode of the invention is shown in FIGS. 1-9. The present invention is premised on having a vertical support column mounted to a wall that may be resting on the floor plane for additional stability and support. The support column is in the form of a support rail 20 as shown in FIG. 6. The support rail 20 is formed of sheet metal with a channel like cross section as shown in FIG. 7. A notable feature of the support rail 20 is that it is the principle load bearing structure that supports the wall mounted unit 10 at any desired height allowing a technician to work standing or seated. Thus, the cabinet assembly wall unit is not as dependent on the location or spacing of the wall studs as the load is supported by the floor or the wall and the pull weight is distributed along the support rail. The vertical sheet metal support rail 20 is initially mounted to a wall using wall anchors and fasteners such as screws which inserted through appropriately spaced apertures 21 cut into the linear "L" shaped side sections 22 of the rail. It should be noted that the thickness of the "L" shaped side sections 22 is greater than the thickness of the center connector section 23 to provide for additional load support. The rail 20 is thus load bearing and the attachment of the rail 20 to the wall 200 can be accomplished with the drilling of 4 to 6 holes using the spacing apertures 21 provided in the rail 20. The rail 20 is formed with central spaced cutouts 24 which allow it to be mounted over an existing wall outlet box allowing the outlet box to be used for power with all of the wiring neatly concealed inside the covered channel 28 of the rail 20. The channel 28 has a depth which is deep enough to permit an electrical junction box to be mounted in the profile of the channel. As noted the support rail defines a plurality of punched cut out openings 24 for receptacle box(es) in its middle base section and additionally has a plurality of spaced apertures 26 located along it linear "L" shaped side sections 22 allowing the housing cover 34 and cover plate 50 to be mounted to the support rail 20. Thus all of the wiring running from the floor to the wall mount unit can be incorporated in the vertical support channel 28 of the mounting rail 20. Wiring may consist of power lines, data lines and the like.

Figure 5:
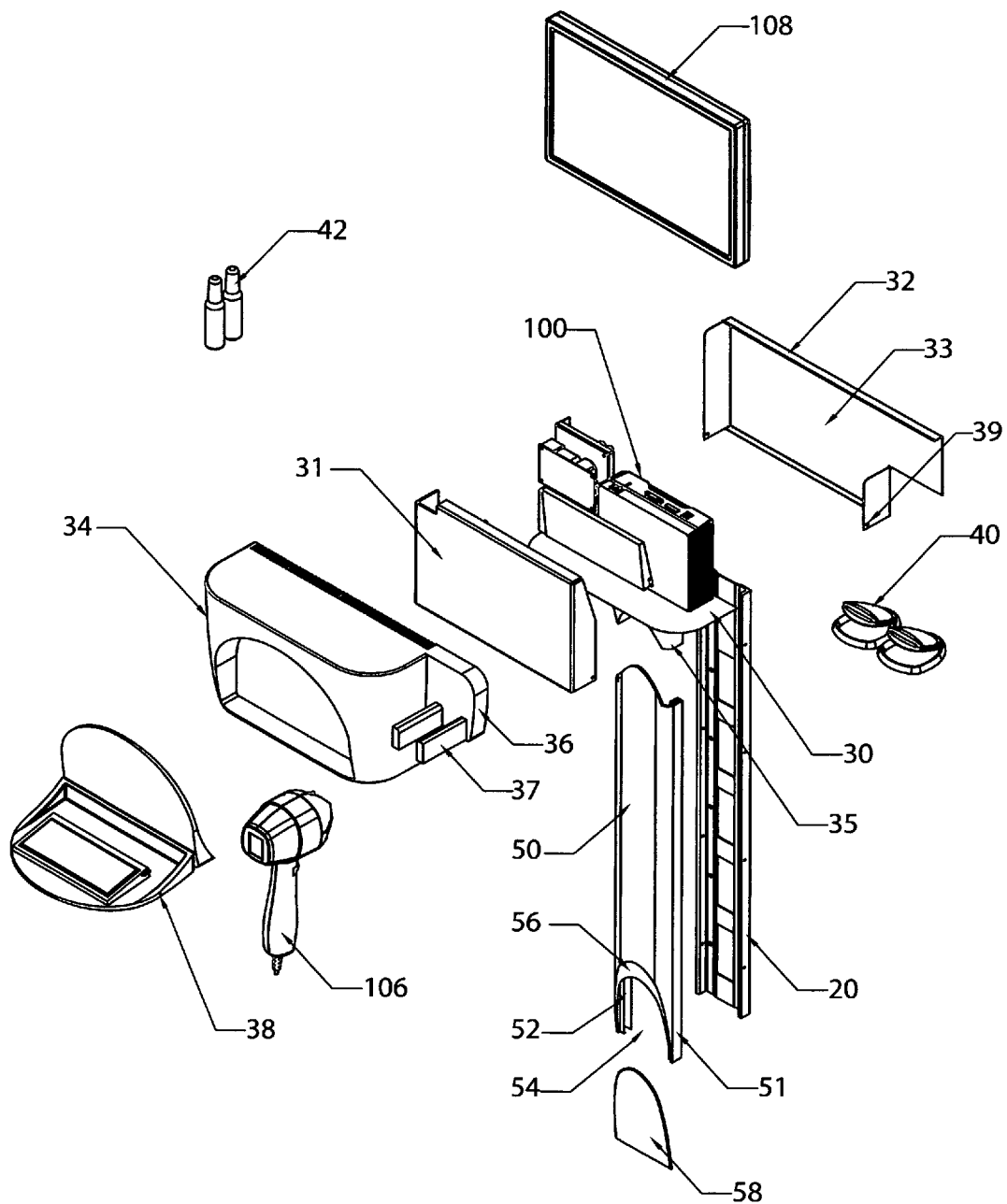
FIG. 5 is an exploded view of the inventive wall mount cabinet assembly of FIG. 1.

A chassis coupler and support assembly 30 is mounted on top of the support rail 20 by fastening a tapered neck support 35 over the support member rail 20 to the wall surface. The chassis coupler assembly 30 is mounted to the rail 20 by appropriate fasteners. A front chassis section member 31 and a rear chassis section member 32 are mounted on the chassis coupler assembly 30. Electronics 100 such as computer systems and other processor equipment are mounted on the coupler assembly 30 top planar surface and housed between front chassis section member 31 and rear chassis section member 32. The rear chassis section member 32 has a flat base surface 33 which can be fastened to the wall surface via mounting apertures. An exterior housing cover 34 is mounted over the coupler assembly 30 and the front and rear chassis section members 31 and 32 and is constructed to hold a keyboard or work surface in the form of a drop down panel 38. Other electronics including power supplies such as USB hub, wiring harnesses, processors, memory devices and the like are housed within the chamber formed by the housing chassis sections and chassis coupler assembly 30. The exterior housing cover 34 defines a probe holding extension 36 on one side formed with a slot mechanism 37 as shown in FIGS. 3-5 which holds a probe 106 or other ancillary components such as optical scanners, transducers, temperature sensors, digital cameras and the like. The housing cover 34 is provided with a drop down panel 38 to support a keyboard, mouse or other input device or simply serve as a work surface. The drop down panel 38 is hinged at 39 as shown in FIG. 1 allowing the panel to be rotated back into the housing cover 34. The top of the housing cover 34 can be also equipped with card readers 40 or other memory or input devices as needed as well as a plurality of receptacles 42 for liquid containers, swabs, cups or additional data ports.

Figure 8:
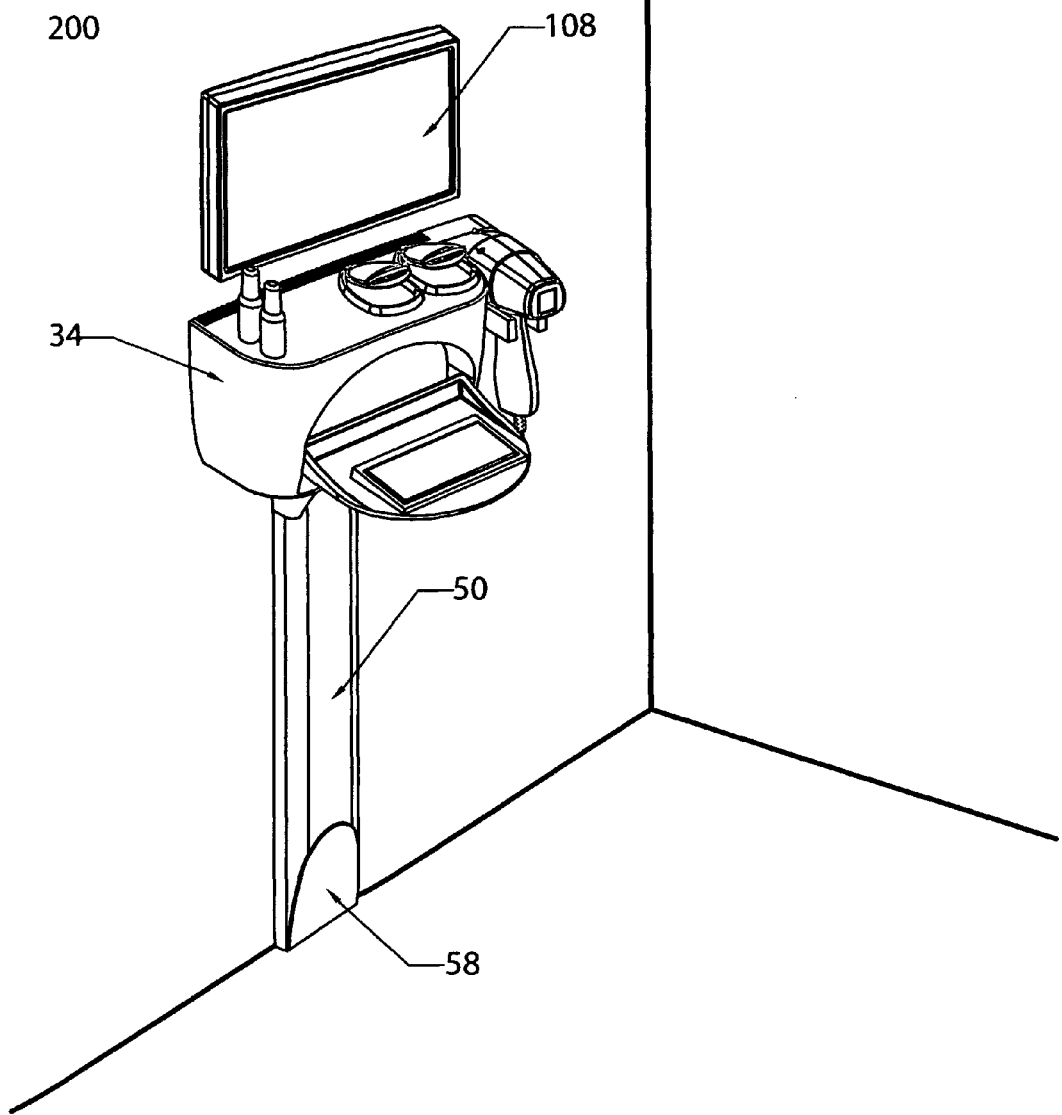
FIG. 8 is a perspective view of the cabinet assembly mounted to the wall of a medical facility.

Rear chassis section member or plate 32 is mounted to the rear of the chassis coupler 30 and can be alternatively provided with a recessed extension shelf 39 for holding a touch screen monitor 108. The rear chassis plate 32 has a flat rear section 33 for fitting flush against the wall and allowing the same to be fastened to the wall. Alternatively, the touch screen monitor 108 can be mounted on the support rail 20 using bracket 110 located on the back of the monitor or mounted to the wall 200 above the cabinet as shown in FIG. 8.

The support rail 20 is covered with a cover plate 50 which may be composed of an aluminum extrusion, sheet metal or plastic which covers the channel of the rail. The cover plate 50 has sides 51 which define two linear raceways 52 on each side of the cover plate 50 which provide for power (110 AC and/or low voltage DC) and cable connections leading from the wall to the electronics used with the cabinet assembly and has a distal end 54 with a curved beveled cutaway 56. The cover plate 50 can be removed if access is needed at any time following installation. The cover plate 50 can be fastened to the rail 20 using the side holes 26 located in the rail sides. An access cover panel 58 may be snap mounted to the cutaway 56 of the cover plate 50 to provide access to the plug or electrical feed area.

Figure 9:
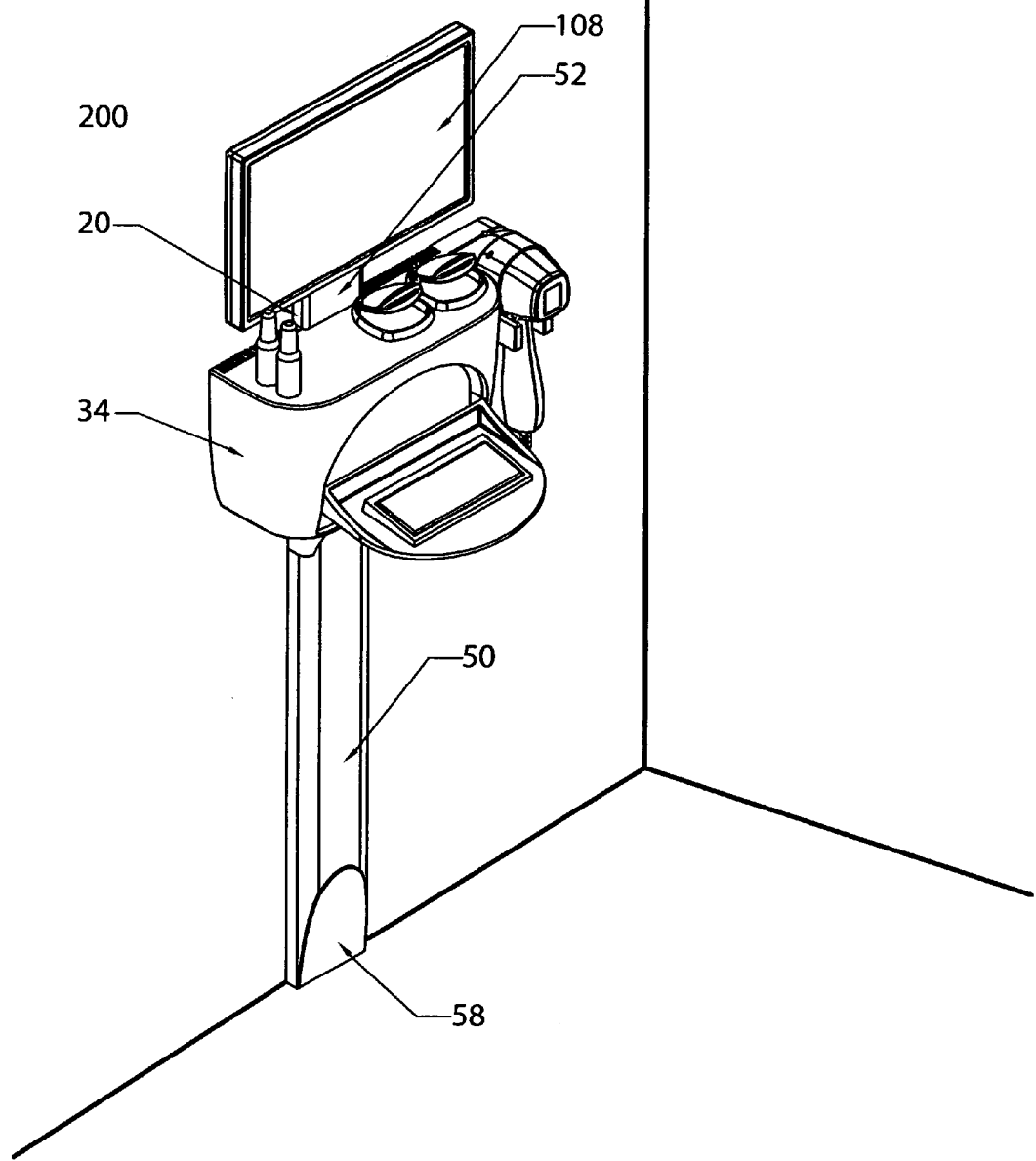
FIG. 9 is a perspective view of the cabinet assembly mounted to the wall of a medical assembly with the display unit mounted to the rail.

As previously noted, it is also envisioned that the display unit 108 can easily be mounted to the wall support rail 20 solving present wall mount problems. Thus the rail 20 can be longer and extend above the work surface of the apparatus to accommodate the display mount 110. A cover plate 52 is mounted on that portion of the support rail 20 which extends above the work surface as is shown in FIG. 9.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. An instrument cabinet assembly comprising
   a) a support rail defining a channel therein, said support rail defining a plurality of spaced cutouts;
   b) a housing support assembly mounted to said support rail;
   c) a housing mounted to said support assembly; and
   d) an exterior cover removably mounted to said housing, and
   e) a drop down panel pivotally mounted to said exterior cover which drops down to a position substantially horizontal to a floor surface.

2. The instrument cabinet assembly of claim 1 wherein said support rail is "U" shaped with spaced cutouts in its base and legs extending outward from each side of said base; said base and said legs defining a plurality of spaced apertures.

3. The instrument cabinet assembly of claim 1 wherein a support rail cover plate is mounted to said support rail.

4. The instrument cabinet assembly of claim 3 wherein said cover plate is linear and defines a cut out distal end and an access plate is removably mounted to said cover plate distal end covering said cut out.

5. The instrument cabinet assembly of claim 4 wherein said cover plate has a linear center section and legs which extend outward from each side of said center section with the width between said legs being dimensioned to fit over said support rail.

6. The instrument cabinet assembly of claim 1 wherein said exterior cover defines a slotted support structure on one end.

7. The instrument cabinet assembly of claim 1 wherein a display unit is mounted to said support rail.

8. The instrument cabinet assembly of claim 1 wherein said housing comprises a rear member with a planar surfaced section and a front housing member which can be mounted on said support assembly.

9. The instrument cabinet assembly of claim 8 wherein said rear housing member defines an extension structure for a touch screen monitor mounting.

10. The instrument cabinet assembly of claim 1 wherein at least one card reader is mounted to said housing.

11. A wall mounted instrument cabinet assembly comprising
   a) a linear support rail comprising a base section with legs extending outward from each side, said base section and legs defining a channel therein, said support rail base section defining a plurality of spaced cutouts sized to fit over power outlets;
   b) a housing support coupler means mounted to said support rail;
   c) a housing mounted to said housing support coupler means; a drop down panel pivotally mounted to said housing which drops down to a position substantially horizontal to a floor; and
   d) a cover plate mounted on said support rail to cover said support rail.

12. The wall mounted instrument cabinet assembly of claim 11 wherein said support rail is substantially "U" shaped with spaced cutouts in its base section and spaced apertures formed in said legs and base section adapted to receive fastening means.

13. The wall mounted instrument cabinet assembly of claim 11 wherein said cover plate is linear and defines a cutout distal end and an access plate removably mounted to said cover plate end covering said cutout.

14. The wall mounted instrument cabinet assembly of claim 11 wherein said cover plate has a center section and legs which extend outward from each side of said center section with the width between said legs being dimensioned to fit over said support rail legs.

15. The wall mounted instrument cabinet assembly of claim 11 wherein said cover plate defines a plurality of wiring raceways.

16. A wall mounted instrument cabinet assembly comprising
   a) a support rail defining a channel therein, said support rail defining a plurality of spaced cutouts and a plurality of spaced apertures;
   b) a housing coupler means mounted to said rail, said housing coupler means comprising a planar support plate and a tapered neck support;
   c) a housing mounted to said housing coupler means; a drop down panel pivotally mounted to said housing which drops down to a position substantially horizontal to a floor; and
   d) a cover plate mounted on said support rail to cover said support rail, said cover plate defining a cut out end and an access panel mounted on said cover plate covering said cut out end.

17. The wall mounted instrument cabinet assembly of claim 16 wherein said cover plate defines a plurality of wiring raceways.

18. The wall mounted instrument cabinet assembly of claim 16 wherein said support rail is substantially "U" shaped with spaced cutouts in its base and spaced apertures are formed in legs extending outward from each side of said base.

19. The wall mounted instrument cabinet assembly of claim 16 wherein said cover plate has a center section and legs which extend outward from each side of said center section with the width between said legs being dimensioned to fit over said support rail side legs.

* * * * *